United States Patent [19]

Eydelman et al.

[11] Patent Number: 5,050,605

[45] Date of Patent: Sep. 24, 1991

[54] MAGNETIC RESONANCE IMAGING ANTENNAS WITH SPIRAL COILS AND IMAGING METHODS EMPLOYING THE SAME

[75] Inventors: Gregory Eydelman, West Hempstead; Anthony Giambalvo, Kings Park; Raymond V. Damadian, Woodbury, all of N.Y.

[73] Assignee: Fonar Corporation, Melville, N.Y.

[21] Appl. No.: 337,041

[22] Filed: Apr. 12, 1989

[51] Int. Cl.⁵ .......................................... A61B 5/055
[52] U.S. Cl. ......................... 128/653 OSC; 324/318; 324/322; 128/653 A
[58] Field of Search ..................... 128/653 A, 653 SC; 324/309, 318, 322

[56] References Cited

U.S. PATENT DOCUMENTS

| | | | |
|---|---|---|---|
| 4,354,499 | 10/1982 | Damadian | 128/653 A |
| 4,608,991 | 9/1986 | Rollwitz | 128/653 A |
| 4,635,643 | 1/1987 | Brown | 128/653 A |
| 4,636,730 | 1/1987 | Bottomley | 324/318 |
| 4,774,468 | 9/1988 | Bydder | 128/653 SC |
| 4,793,356 | 12/1988 | Misic et al. | 128/653 SC |

FOREIGN PATENT DOCUMENTS 0127705 7/1985 Japan ........................ 128/653 SC

OTHER PUBLICATIONS

Sobol, Wladyslaw, "Dedicated Coils in Magnetic Resonance Imaging", Reviews of Magnetic Resonance in Medicine, vol. 2, No. 2, pp. 181-224, 1986.

Primary Examiner—Lee S. Cohen
Assistant Examiner—John D. Zele
Attorney, Agent, or Firm—Lerner, David, Littenberg, Krumholz & Mentlik

[57] ABSTRACT

An antenna structure for magnetic resonance imaging includes a plurality of spiral wound, generally planar coils spaced axially from one another. The plural coils may be mounted on a rigid frame in the desired relative positions and the subject may be inserted in the space defined by the frame. Alternatively, the individual coils can be separately supported on the subject, as by mounting the coils to the subject. Desirably, a part of the subject's body extends through central apertures in one or more of the coils.

26 Claims, 4 Drawing Sheets

MAGNETIC RESONANCE IMAGING ANTENNAS WITH SPIRAL COILS AND IMAGING METHODS EMPLOYING THE SAME

The present invention relates to the art of magnetic resonance imaging, also referred to as nuclear magnetic resonance imaging.

Magnetic resonance imaging or "MRI" provides images of internal structures of a subject without the need for X-rays or other invasive techniques. Magnetic resonance imaging uses the phenomenon referred to as nuclear magnetic resonance. Certain atomic nuclei have spins. In the presence of a strong magnetic field, these spins tend to align themselves in the direction of the magnetic field. Upon exposure to radio waves having particular frequency, referred to as the resonant or Larmor frequency, the vectors of the nuclei are displaced out of alignment with the applied magnetic field. After such displacement, the spins of the nuclei turn or "precess" around the direction of the applied magnetic field. As each spin turns, the nucleus creates an infinitesimal radio signal, referred to herein as a "magnetic resonance signal", also at the resonant or Larmor frequency. The precessing spins gradually drift out of phase with one another, and gradually drift back into alignment with the direction of the applied magnetic field. Therefore, the magnetic resonance signals gradually decay. Certain parameters of the magnetic resonance signals vary with the chemical and physical state of the matter being studied.

In magnetic resonance imaging, the properties of magnetic resonance signals from individual small volume elements or "voxels" within a larger subject are determined. This permits generation of an image such as a pictorial image representing individual volume elements having differing chemical and/or physical properties in contrasting shades. Because the magnetic field and exciting radio frequency signal typically are applied to a sizable region of the subject, far larger than each individual volume element, it is necessary to apply some technique for identifying the magnetic resonance signals from different volume elements. Techniques for encoding magnetic resonance signals spatial information and determining the magnetic resonance parameters of individual volume elements from signals representing many volume elements are complex and beyond the scope of this disclosure. However, these techniques are well known to those in the magnetic resonance imaging arts.

Because MRI can generate images based on chemical and physical variations in the body of the subject, magnetic resonance imaging can depict essentially any tissue in a living subject such as a human. MRI does not rely upon absorption of X-rays or other ionizing radiation by the body tissue. Moreover, MRI can detect abnormalities which are extremely difficult or impossible to detect by other techniques. Therefore, MRI has been widely adopted in the medical profession.

The magnetic resonance signals generated by the subject are extremely weak. To obtain a useful image, these signals must be received and distinguished from background electromagnetic noise. Typically, the magnetic resonance signals are converted to electrical impulses by an antenna and conveyed to the preamplifier of a radio frequency receiver adapted to amplify and detect signals at the resonant frequencies of interest. The information recovered by this receiver is conveyed to known devices for digitizing the signals and processing the digitized signals to recover the image. The quality of the image is directly related to the quality of the receiving antenna. One measure of antenna quality is sensitivity, i.e., the signal voltage generated in the receiving antenna by magnetic resonance signals of a particular magnitude. The higher the sensitivity within the region to be imaged, the weaker the signals which can be detected. Desirably, the sensitivity of the antenna is substantially uniform with respect to magnetic resonance signals emanating from all volume elements within the region of the subject which is to be imaged. Another measure of antenna quality is signal to noise ratio, i.e., the ratio between those components in the electrical impulses appearing at the antenna terminals representing the desired magnetic resonance signals to the components representing spurious electromagnetic signals in the environment. To optimize the signal to noise ratio, the antenna should have low sensitivity to signals from outside the region to be imaged. To enhance both signal to noise ratio and sensitivity, the antenna should be "tuned" or arranged to resonate electrically at the frequency of the magnetic resonance signals to be received, typically several megaHertz or more. As further discussed below, this implies certain limits on the electrical characteristics of the antenna such as its inductance and capacitance.

Moreover, the antenna should be compatible with the physical requirements of the system. The magnet assemblies employed to generate the magnetic field applied to the subject typically provide relatively small spaces for receiving the subject within the magnet assembly. The receiving antenna must fit within this limited space together with other components of the system and the subject. The receiving antenna should not impose any particularly difficult physical constraints on the subject. In the case of a human or animal subject, the antenna should not cause significant discomfort to the subject. Additionally, the antenna structure should be easy to use and relatively insensitive to minor faults in positioning relative to the subject. These numerous considerations often conflict with one another and together present a formidable problem.

Substantial efforts have been made heretofore in design of magnetic resonance imaging antennas. As disclosed, for example, in Sobol, "Dedicated Coils in Magnetic Resonance Imaging", *Reviews of Magnetic Resonance in Medicine*, Vol 1, No. 2, pp. 181–224, 1986, certain electrical properties such as the pattern of sensitivity for a particular antenna can be calculated with reasonable accuracy from mathematical treatment of the parameters describing antenna design after the design has been specified. The same properties can be measured experimentally after the antenna has been built. As further discussed in the same article, the antenna configurations which have been tried include single flat loops of conductive wire, dual loops coaxial with one another and spaced apart along their common axis, commonly referred to as a Helmholtz pair, solenoidal or helical coils and saddle-shaped coils. Some of these coils are mounted to the magnet structure so that the coil is adjacent the patient receiving space of the magnet structure and receives signals from substantially the entire patient receiving space. Thus, saddle-shaped coils can be mounted within a cylindrical bore of a typical cylindrical, air core solenoid magnet structure used in some MRI equipment.

Other coils are mounted in close proximity to the patient's body. For example, it has been the practice heretofore to employ solenoidal coils extending in helical fashion around the patient's body or around an anatomical feature of interest such as the head or a limb. Coils extending generally along the surface of the subject's body are commonly referred to as "surface coils". Surface coils of this nature can be used to receive signals from within the encircled region of the subject's body. Because solenoidal surface coils are sensitive principally to signals originating in the encircled region they tend to reject spurious signals and hence to provide a relatively high signal to noise ratio. As disclosed in co-pending, commonly assigned U.S. patent application Ser. No. 257,399, filed Oct. 13, 1988, the sensitivity uniformity of such solenoidal surface coils can be enhanced by increasing the length or axial extent of the coil. Although the sensitivity of the solenoidal surface coil can be enhanced by increasing the number of turns in the solenoidal coil, the number of turns in any such coil is necessarily limited by considerations of excessive inductance and capacitance which would make it impossible to tune the coil to the resonant frequency. Moreover, solenoidal coils cannot be applied practically to every region of a typical patient. For example, it is difficult in some cases to apply a small solenoidal surface coil around a patient's shoulder. Further, solenoidal surface coils can be uncomfortable for some patients when the coil is applied around the patient's head.

Other surface coils have been made in the form of small, generally planar wire loops such that the entire loop can be arranged on the patient's body surface in an area overlying an anatomical feature of interest. In such an arrangement, the looplike coil lies substantially in the plane of the body surface. Although coils of this nature provide useful signals for imaging structures lying close to the skin, they suffer from a very significant drawback in that their sensitivity decreases dramatically with distance from the plane of the coil loop. Thus, this type of surface coil is essentially useless for imaging structures deep within the body.

Brown, M.E. et al., The Design Construction and Evaluation of Receiver Coils for Specific MR Imaging Application, in the Book of Abstracts, Fifth Annual Meeting, Society of Magnetic Resonance in Medicine, Addenda, Works-in-Progress, pp 43-44, 1986, mentions an antenna structure including two spiral coils spaced axially from one another. These coils are spaced from one another so that small body parts such as hands and ankles can be inserted in the gap between the two spaced coils. The dual-coil design is expressly characterized in this article as limited to imaging of small body parts.

Accordingly, despite all of the effort expended heretofore in development of MRI receiving antennas, there are still considerable unmet needs for further improvements in MRI receiving antenna structures and in methods of using the same.

SUMMARY OF THE INVENTION

The present invention addresses these needs. One aspect of the present invention provides a receiving antenna for a magnetic resonance imaging system. An antenna according to this aspect of the present invention includes a first spiral coil having an axis and having radial directions transverse to the axis. The first spiral coil desirably has an aperture adjacent the axis and a plurality of turns of progressively varying radial extent encircling the aperture. Thus, the first spiral coil may include an innermost turn closest to the axis, and hence closest to the aperture, and may also include one or more outer turns at progressively greater distances from the axis and aperture. The antenna desirably also includes means for positioning the first spiral coil adjacent the body of a subject to be imaged so that the body part extends through the aperture and the turns of the first spiral coil encircle the body part. Thus, the outer turns having progressively larger radial extent will be disposed at progressively greater distances from the surface of the encircled body part. The antenna desirably includes means for connecting the first spiral coil to an input of a radio receiver.

The antenna may further include additional antenna elements such as a second spiral coil and optionally a third spiral coil. Still further additional antenna elements may be included.

Positioning means may include a frame and both of the coils may be mounted to the frame so that the frame holds the coils in substantially predetermined spatial relationship to one another. The coils and the frame may cooperatively define a structure having a patient receiving space between the coils. The aperture in the first may provide an opening for insertion of the body part into the patient receiving space of the structure. Desirably, the frame is arranged so that the axes of the coils are substantially parallel to one another and so that the coils substantially overlie one another but are spaced apart from one another in their respective axial directions. Alternatively, each of the plural spiral coils may be provided with separate fixtures for supporting the coils on the body of the subject, and thus maintaining the coils in the desired spatial relationship to one another. The second spiral coil may have an aperture adjacent its axis such that the turns of the coil encircle the aperture, and the apertures in the second coil may define one or more of the openings in the coil and frame structure. The apertures in the coils may be aligned with one another, so that an elongated body part may extend through the aligned apertures. Additional openings may be provided by openings in the structure adjacent one of the coils, such as axial gaps between the coils. Alternatively, the additional antenna element or second coil may have structures such as inner turns disposed adjacent its axis, so that this structure or inner turns of the second coil may be aligned with the axis and aperture in the first coil. In use, the additional antenna element may overlie an end or distal surface of a body part which extends through the aperture in the first coil.

A further aspect of the present invention provides methods of magnetic resonance imaging including the steps of providing an antenna including first spiral coil as aforementioned, positioning this spiral coil adjacent the body of a subject to be imaged so that a body part of the subject extends through the aperture in the first coil and the turns of this coil encircle this body part. Desirably, the method further includes the step of positioning one or more additional antenna elements such as further spiral coils adjacent the body of the subject and within interactive range of the first coil. As further discussed hereinbelow, plural antenna elements may be said to lie in interactive range of one another when they are close enough to one another such that there is substantial interaction between each coil and the magnetic field from the other coil. Most preferably, the positioning step is performed so that the axes of plural spiral coils lie substantially parallel to one another and so that the coils overlap one another. Thus, the plural spiral coils may be positioned substantially coaxial with one another. The positioning step may be performed by mounting the spiral coils to the body surface of the patient or else may be performed by positioning the appropriate region of the patient in the patient receiving space of a coil and frame structure as mentioned above.

The method further includes the steps of exciting nuclear magnetic resonance in the body of the subject and receiving magnetic resonance signals from the subject by way of the coil or coils and reconstructing an image of at least a part of the body of the subject from the received resonance signals.

Preferred methods and apparatus according to the present invention provide unique combinations of high sensitivity and high signal to noise ratio with deep penetration, i.e., with good sensitivity to magnetic resonance signals from regions deep within the body. Moreover, preferred methods and apparatus according to the present invention provides antenna structures and methods of using the same which are versatile in that they can be applied to almost any area of a typical subject. Additionally, the structures and methods according to preferred embodiments of the present invention provide these enhanced results while maintaining practical values of antenna inductance and capacitance, thereby facilitating tuning of the antenna to the resonant frequency. Further, preferred structures and methods according to these aspects of the present invention combine these desirable results with excellent convenience in use and with excellent patient comfort.

These and other objects, features and advantages of the present invention will be more readily apparent from the detailed description of the preferred embodiments set forth below, taken in conjunction with the accompanying drawings.

DETAILED DESCRIPTION OF THE PREFERRED EMBODIMENTS

Figures 1, 2:
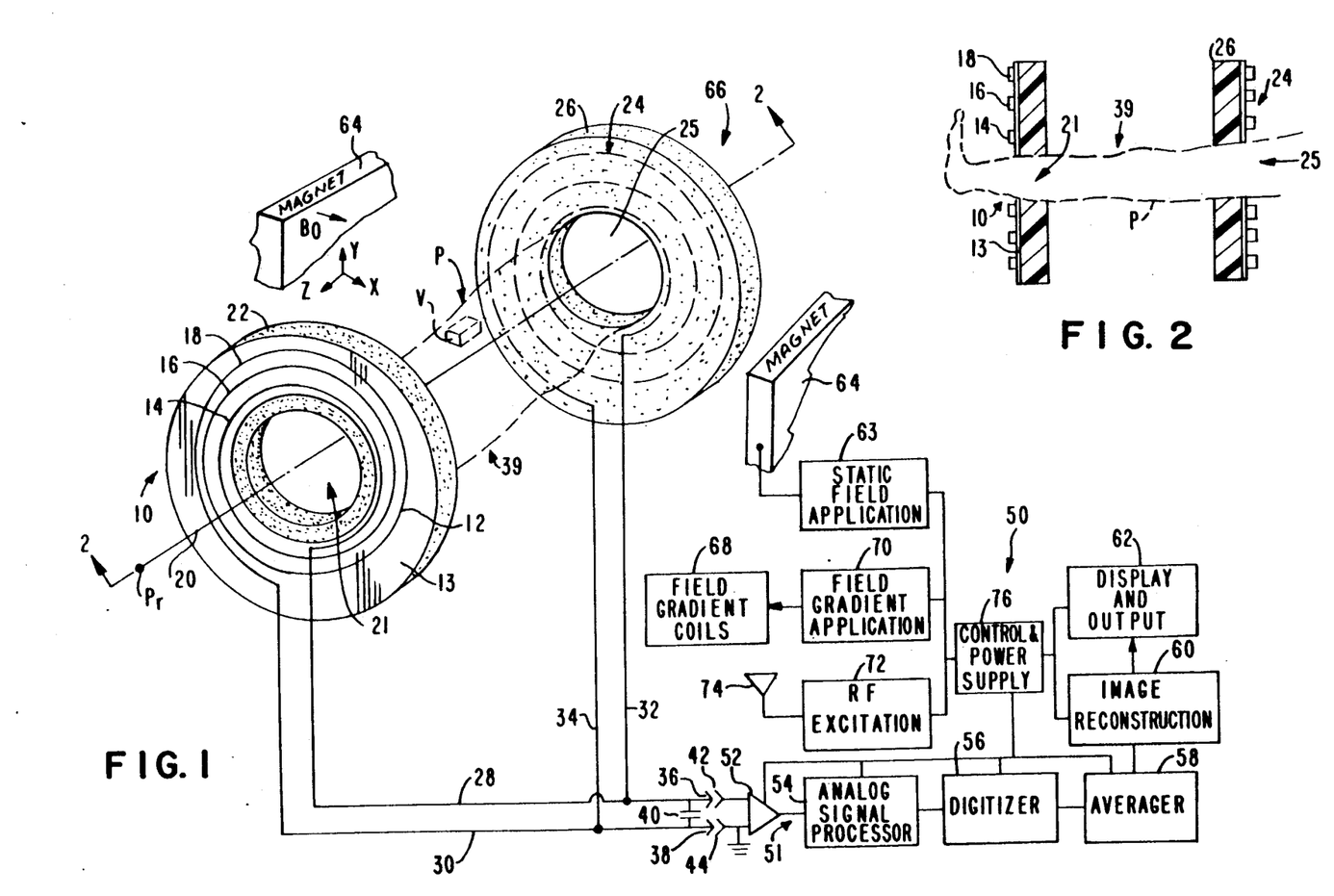
FIG. 1 is a schematic view depicting an antenna in accordance with one embodiment of the present invention, in conjunction with a subject to be imaged and with other elements of a magnetic resonance imaging system.
FIG. 2 is a schematic sectional view taken along lines 2—2 in FIG. 1.

An antenna in accordance with one embodiment of the present invention includes a first spiral coil 10. Coil 10 includes a single metallic conductor 12 which in this case is a copper strip disposed on a sheetlike polymeric support. The conductor 12 extends through three turns 14, 16 and 18 around a central axis 20. Turns 14, 16 and 18 are of progressively varying size or extent in the radial directions transverse to axis 20. Thus, turn 14 is the radially innermost turn, lying closer to axis 20 than any of the other turns 16 and 18, whereas turn 16 is an intermediate turn and turn 18 is the radially outermost turn, lying at the greatest radial distances from the axis. The innermost turn 14 lies at a substantial distance from axis 20 and hence defines an aperture 21 inside the innermost turn and encompassing axis 20. Coil 10 defines a generally spiral shape in the sense that its turns are of progressively increasing radial extent. Each portion of turn 16 is disposed at greater radial distance from axis 20 than the corresponding portion of coil 14 and likewise each portion of outermost turn 18 is disposed at a greater radial distance from axis 20 than is the corresponding portion of intermediate turn 16. As used in this disclosure, the term "spiral" as used with reference to a coil should be understood as encompassing a coil having this geometric property of progressively varying radial extent on successive turns regardless of whether the dimensions in the radial direction vary monotonically or continuously along the length of the conductor.

As further discussed hereinbelow, the radial extent of a coil can be significant in describing the spacings and functions of the coil. One such measure of the radial size of a spiral coil is the mean outer radius, the average value of the radial distance for the outermost turn. Another useful measure is the mean radius of the coil, i.e., the mean of radial distance for all points on the conductor constituting the coil, over all of the turns. As seen in FIG. 2, coil 10 lies in or close to a plane transverse to the central axis 20. The term "generally planar" as used in this disclosure with reference to spiral coils refers to a coil in which the axial extent of the coil—the maximum distance parallel to the axis of the coil between any two points on the conductor—is less than about 25% of the mean outer radius of the coil. Coils intended to encircle a part of the subject desirably are as close to planar as is practicable, and hence may have a maximum axial extent less than 10% and in some cases less than 5% of the outer radius.

Coil 10 is mechanically fastened on a ring-shaped pad 22 of an electrically non-conductive, relatively soft foam material attached to support 13. Pad 22 extends radially inwardly slightly beyond the radially innermost margin of support 13, and hence extends radially inwardly into aperture 21. The antenna further includes a second spiral coil 24. Coil 24 is substantially identical to coil 10. Coil 24 defines a central aperture 25 and is attached to a ringlike foam pad 26 protruding slightly into aperture 25.

Additionally, the antenna includes leads 28 and 30 connected to the innermost and outermost ends respectively of first coil 10 and leads 32 and 34 connected to the innermost and outermost ends respectively of second coil 24. The leads are connected to one another and to connectors 36 and 38 so that coils 10 and 24 are in parallel with one another across connectors 36 and 38. The pattern of interconnection of the leads and connectors is selected so that when the coils 10 and 24 are positioned with the associated foam pads 22 and 26 toward one another (as seen in FIGS. 1 and 2) current passing from connector 36 to the connector 38 will flow either clockwise or counterclockwise in both coils, as viewed by an imaginary observer at a common reference point $P_r$ on axis 20 outside of the gap 39 between the two coils. For example, current passing from connector 36 to connector 38 will pass counterclockwise in each of coils 10 and 24 as seen by an imaginary observer at point PR. The term "connected for codirectional current flow" is used in this disclosure as referring to plural coils interconnected so as to meet this condition. As will be appreciated, it is not necessary that the directions of windings of the plural coils be the same as one another in order for the plural coils to be interconnected for codirectional flow. Merely by way of example, if the direction of winding of one of the coils 10 or 24 were reversed, that reversed coil could still be interconnected for codirectional current flow with the other if the leads extending to one coil were modified to reverse the leads as between the innermost and outermost ends of the coil.

A capacitor 40 is connected across connectors 36 and 38, and hence in parallel with the parallel connected coils 10 and 24. Connectors 36 and 38 are arranged to mate with the input signal and ground connectors 42 and 44 of a radio signal receiving section 51 of a magnetic resonance imaging unit 50. Although leads 28–34 and capacitor 40 are depicted and referred to separately for clarity of illustration, it should be appreciated that all or a portion of the capacitance 40 in parallel with the coils may be contributed by parasitic capacitances of the coils themselves and/or capacitance in the leads 28–34. Desirably, leads 28 and 30 are constituted of a single coaxial cable, whereas leads 32 and 34 are formed as another coaxial cable to minimize the effects of stray electromagnetic radiation on the leads. In this arrangement particularly, there may be substantial capacitance between the leads.

The antenna is employed in conjunction with a magnetic resonance imaging apparatus 50. Imaging apparatus 50 may include a radio signal receiver 51 including a preamplifier 52 for receipt and amplification of magnetic resonance signals in the form of electrical voltages and a further analog signal processing section 54 adapted to take the amplified signals from preamplifier 52. Analog signal processing section 54 may include conventional amplification, filtering and demodulation and/or mixing devices. The MRI unit 50 further includes a digitizer 56. Digitizer 56 is adapted to convert the magnetic resonance signals processed by analog signal processor 54 into digital form. The output of digitizer 56 is connected to the input of an averager 58 arranged to average a plurality of digitized signals. The imaging apparatus may further include an image reconstruction computer 60 arranged to derive an image from the signals averaged by averaging unit 58. Image reconstruction unit 60 is linked to a display and output unit arranged to show the image in a human-readable form such as a pictorial display and also to output the image to appropriate storage or communications devices (not shown).

Additionally, the magnetic resonance imaging unit 50 includes a static magnetic field application unit 63 which incorporates a large magnet 64, schematically and fragmentarily illustrated in FIG. 1. Magnet 64 defines a patient receiving space 66, the magnet being adapted to apply a substantially uniform static magnetic field $B_O$ within space 66. Space 66 is large enough to receive at least a portion of a typical human body, preferably large enough to receive the torso and/or the head of a typical human subject. Additionally, the magnetic resonance imaging unit 50 includes a magnetic field gradient coils 68, of which only one is shown in FIG. 1. Typically, three sets of coils are mounted adjacent the patient receiving space 66 of magnet 64, the different sets of coils being arranged on different geometric axes. A field gradient application control unit 70 is provided for selectively energizing the various sets of gradient coils 68 to impose magnetic field gradients or variations in the magnitude of magnetic field $B_O$ on any one or more of the three coordinate axes X, Y and Z. Field gradients can be provided in directions oblique to these axes by preapplying gradients on two axes simultaneously.

Magnetic resonance imaging unit 50 further includes an excitation radio frequency transmitter 72 connected to a transmitting antenna 74 disposed adjacent patient receiving space 66 of magnet 64. All of these components in MRI scanning unit 50 are connected to a control and power supply unit 76 adapted to energize and control all of these components. Typically, the control and power supply unit incorporates a programmed, general purpose digital computer.

The components of MRI scanning unit 50 are conventional and well known, and hence will not be described in detail in this disclosure. Suitable MRI units are made and sold commercially under the trademarks FONAR, BETA 3000 and BETA 3000M by the Fonar Corporation of Melville, N.Y.

In an imaging method according to one embodiment of the invention, first coil 10 and second coil 24 are juxtaposed with a part of the body of a subject such as a leg P of a human patient so that the leg is received in the apertures 21 and 25 of the coils. The coils are positioned at desired locations adjacent the body by foam pads 22 and 26 which engage the surface of the leg. The coils are positioned so that their axes are substantially parallel and approximately coincident, on axis 20.

In this regard, it is not essential that the axes of the coils be exactly parallel or coincident. However, the coils should be arranged in substantially overlapping disposition. As used in this disclosure, a first coil and a second coil may be said to substantially overlap one another if the areas enclosed by their outermost turns, projected parallel to the axis of the first coil into a plane perpendicular to the axis of that coil would intersect one another greater than about 50% of the projected area of the first coil. For example, in the embodiment of FIGS. 1 and 2, the entire area enclosed by the outermost turn of first coil 10 and second coil 24, if projected along the common axis 20 into a common plane perpendicular to axis 20 would intersect. The coil arrangement thus tends to minimize stray capacitance between the coils and the subject's body. As best seen in FIG. 2, coils 10 and 24 are positioned such that the planes of the coils are substantially perpendicular to the adjacent portions of the patient's body surface. Thus, the innermost winding of each such coil is interposed between the outer windings and the patient's skin surface. In effect, the inner windings at least partially shield the subject's body from any electrostatic fields emanating from the outer windings. Further, the outer windings are spaced at greater distances from the patient's body surfaces. Thus, the windings of coils 100 and 102 do not appreciably interact electrostatically with the subject's body and hence do not add substantial stray capacitance to the antenna structure. The turns of each coil 10 and 24 desirably are constituted by thin, striplike metallic elements lying substantially in the plane of the coil and hence lying substantially in a plane perpendicular to the axis of the coil. Such thin, striplike elements may be formed, for example, by a common printed circuit techniques. Where such thin, striplike elements are employed, the capacitance of the coils with respect to the body surface is further limited in that the conductors lie substantially in a plane perpendicular to the body surface of the subject. This minimizes the area of the conductor constituting the innermost coil confronting the surface of the subject's body.

Moreover, the coils are disposed in interactive range of one another, i.e., close enough that there can be appreciable interactions between the two coils. As used in this disclosure, the statement that the two coils lie within interactive range of one another means that the center to center distance between the two coils is less than about 2 times the mean outer radius of the larger one of the two coils (or less than about 2 times the mean outer radius of each coil if both are equal). However, the two coils desirably are spaced apart from one another, so that the center to center distance is more than about 0.5 times the mean outer radius and preferably more than 1 times the mean outer radius.

The subject, and hence the coils supported on the subject are positioned in the patient receiving space 66 of the magnetic resonance imaging system, between the pole 64 of the static field application unit. Preferably, the subject, and hence the coils, are positioned so that the axes of the coils, on common axis 20, lie transverse to the direction the magnetic field vector $B_O$ of the magnetic field 63 generated by magnet 64. With the patient and coils so positioned, MRI unit 50 is actuated to conduct imaging routines in the normal manner. Thus, field gradient application unit 70 is operated to superimpose magnetic field gradients on the static magnetic field, whereas RF transmitter 72 is operated to apply radio frequency electromagnetic radiation to the subject at a frequency corresponding to the resonant or Larmor frequency of the atomic nuclei to be studied in the area of interest. Responsive to this radio frequency excitation, the atomic nuclei in the area of interest radiate electromagnetic radiation or magnetic resonance signals. The gradients applied by unit 70 and the frequencies applied by RF excitation unit 72 are selected according to well known and conventional techniques so that the magnetic resonance signals emitted by the atomic nuclei in the subject are spatially encoded, i.e., so that the information incorporated in the signals, together with information about the gradients and RF signals applied, is sufficient to permit identification of one or more parameters of the magnetic resonance response emanating from one or more particular elements of volume V at known positions within the subject. Typically, but not necessarily, the spatial encoding is performed so that one or more parameters of the magnetic resonance response from a plurality of different volume elements can be identified.

The magnetic resonance signals emitted by the matter within the subject impinge upon the turns of coils 10 and 24, and induce potentials in these coils, which potentials are applied across the input terminals 42 and 44 of receiver preamplifier 52 in the magnetic resonance imaging system 50. These signals are processed in the conventional manner by system 50 to form an image of at least a portion of the subject. Where the spatial encoding process is conducted so that the received magnetic resonance signals incorporate information relating to a plurality of volume elements, the image typically is displayed as a pictorial representation of a magnetic resonance response parameter versus position. Such an image resembles a photograph of a cross section of the subject, except that the contrast or color variation represents differences in magnetic resonance response parameter rather than differences in optical parameters. Techniques for reconstructing images from magnetic resonance signals are well known and conventional, and accordingly will not be described in detail herein. Such techniques are described, inter alia. in the text *NMR Imaging in Biomedicine*, Mansfield and Morris, Eds., 1982, Academic Press, Inc.

Coils 10 and 24 cooperatively provide good sensitivity to magnetic resonance signals from all volume elements between the coils. Thus, for all volume elements disposed within the patient in the gap 39 between the planes of the coils and at a radial distance from axis 20 less than about 1–1.5 times the mean outside radius of the individual coils, magnetic resonance signals from these volume elements will produce appreciable voltages across input terminals 42 and 44. This is so even though the sensitivity for a single one of the two coils diminishes rapidly with distance in the axial direction away from the coil. Although the present invention is not limited by any theory of operation, it is believed that the particularly good spatial distribution of sensitivity in the axial direction results at least in part from an inductive coupling or "transformer" effect between the two coils.

The antenna as shown in FIGS. 1 and 2 provides good sensitivity even for signals emanating from volume elements adjacent axis 20, deep within the body part of leg P. Although the antenna as shown in FIGS. 1 and 2 has appreciable inductance, its inductance typically is less than the inductance of a solenoidal antenna which provides a comparable sensitivity distribution. The parallel connection of the spiral coils reduces the inductance of the antennas shown in FIGS. 1 and 2. By contrast, in an ordinary solenoidal antenna all of the turns are in series and hence their inductances are additive. The relatively low inductance of the antenna facilitates tuning to the desired resonant frequency. The resonant frequency f of a parallel-connected inductance L and capacitance C is given by the well-known formula:

$$f = \frac{1}{2\pi} \frac{1}{\sqrt{LC}}$$

Thus, the lower inductance values permit tuning to a relatively high frequency f even where irreducible stray capacitance implies a relatively high value of C. Notably, this system combines good sensitivity to the desired signals with good localization of the sensitive region. Thus, the antenna system has very low sensitivity to signals remote from the area between the coils. The sensitivity is well localized to a relatively small region of the subject encompassing the area of interest of the subject, between the coils. This materially aids in maintaining an acceptable signal to noise ratio. Further, the antenna system as shown in FIGS. 1 and 2 combines these benefits with ease of use and patient comfort. Thus, the coils positioned on the patient's leg do not create any significant discomfort. Also, the planar coils can be slipped over the distal end of the patient's limb without difficulty.

Figures 3, 4:
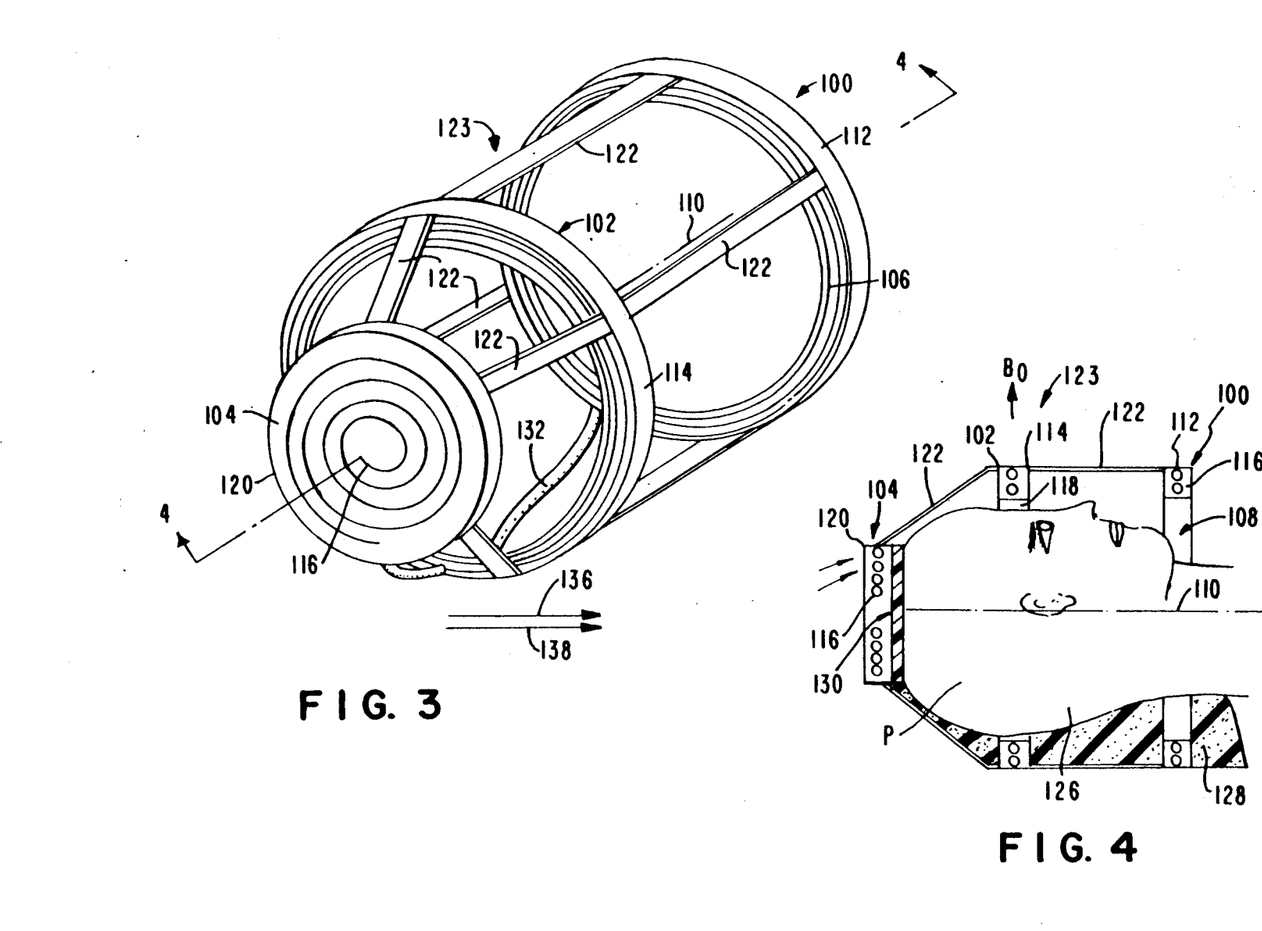
FIG. 3 is a schematic perspective view depicting an antenna in accordance with a further embodiment of the invention.
FIG. 4 is a schematic sectional view taken along lines 4—4 in FIG. 3, but showing the antenna in conjunction with a subject.
Figure 5:
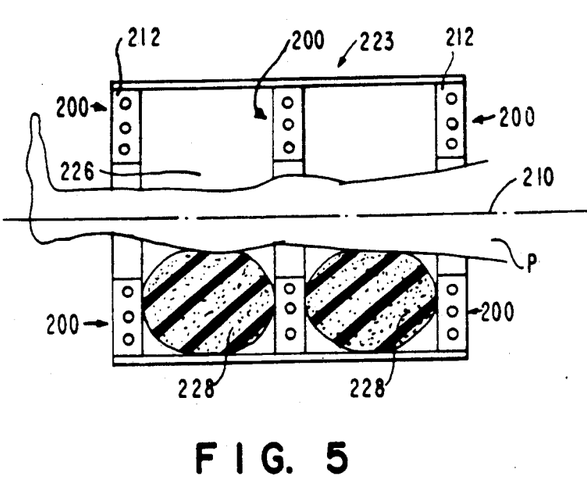
FIGS. 5 and 6 are schematic sectional views depicting antennas in accordance with further embodiments of the invention.

An antenna according to a further embodiment of the invention includes a first coil 100, second coil 104 and third coil 102 (FIGS. 3–5). Coils 100 and 102 are identical to one another. Each of these coils incorporates a conductor arranged to form two generally circular turns of gradually increasing radius. The innermost turn 106 has an substantial radius, and hence coil 100 defines a large aperture 108 adjacent the axis 110 of the coil. Coil 100 is arranged on an annular electrically non-conductive, rigid thermoplastic ring 112. Ring 112 does not substantially occlude the aperture 108 defined by the coil. Coil 102 is likewise arranged on a similar ring 114.

Coil 104 incorporates four turns. The mean radius of the innermost turn 116 of coil 114 is considerably smaller than the mean radii of the innermost turns of apertured coils 100 and 102. Thus, coil 104 is an end coil having its innermost turn 116 close to the axis of the coil. Further, the mean outer radius of coil 104 is considerably smaller than the mean outside radii of coils 100 and 102. As illustrated, the mean outer radius of coil 104 is smaller than the radius of the apertures 108 and 118 defined by coils 100 and 102 respectively. Coil 104 is mounted on a rigid, electrically non-conductive plate 120. Plate 120 and rings 112 and 114 are interconnected by a plurality of support bars 122. Support bars 122, rings 112 and 114 and plate 120 cooperatively constitute a substantially rigid frame 123 which maintains coils 100, 102 and 104 in predetermined spatial relationship to one another such that the axes of all coils 100, 102 and 104 are substantially coincident on a common axis 110 and such that the coils are axially spaced from one another with third coil 102 lying axially between first or apertured coil 100 and third or end coil 104. Each pair of mutually adjacent coils 102 and 100 and 102 and 104 are within interactive range of one another. Moreover, all of the coils substantially overlap one another.

Bars 122 are spaced around the common coil axis 110 so that the frame is generally cage-like with significant open gaps between the rings and plates and between the bars 122. The frame 123, cooperatively with the coils thus forms an open structure having a patient receiving space 126 encompassing the common axis 110 in the region axially between the first apertured coil 100 and the second or end coil 104. A cushion formed from an electrically non-conductive, non-magnetic material such as a foamed plastic 128 is disposed within patient receiving space 126, bearing on rings 112 and 114 to one side of axis 110. A further, similar cushion 130 is disposed adjacent plate 120. These cushions are omitted from FIG. 3 for clarity of illustration.

Coils 100, 102 and 104 are connected in parallel with one another by coaxial cables 132 extending between these coils. Cables 132 incorporate substantial capacitance. The centrally disposed coil 102, and hence the other parallel-connected coils are connected to a pair of plugs 136 and 138, adapted for connection to the magnetic resonance signal inputs 42 and 44 of the MRI imaging unit 50 (FIG. 1). In a further method according to the present invention, a portion of a subject, such as the head of a patient P is positioned within the patient receiving space 126 defined by the antenna structure. The head is supported on cushions 128 and 130 and thus juxtaposed with the coils 100, 102 and 104 with apertured coils 100 and 102 encircling the head and end coil 104 confronting the top distal end surface of the head. Cushion 130 maintains cap coil 104 at a predetermined, small gap, typically about 1.0 cm., from the skin surface. Typically, the patient lies in a horizontal position as shown, so that the patient's head is supported by cushion 128. The antenna structure, and the other body portions of the patient, are supported on a conventional table (not shown) which in turn is inserted into the magnet 64 of the MRI imaging system (FIG. 1) so that the common coil axis 110 is transverse to the magnetic field vector $B_o$. The magnetic resonance imaging apparatus is actuated as discussed above.

The coil assembly as discussed with reference to FIGS. 3 and 4 provides excellent sensitivity in the regions adjacent the common coil axis 110 over the axial region between coils 100 and 104. The sensitivity is especially good in the regions from cap coil 104 to a point about axially midway between coils 102 and 100. This distribution of sensitivity is particularly well matched to the requirements for MRI imaging of the brain and neighboring structures within the human head. Moreover, these results are provided in an antenna structure which still provides good levels of patient comfort. In particular, the gaps between the coils substantially avert the claustrophobic feeling associated with antenna structures which closely cover the head and which provide at most relatively small gaps between antenna structures. Additionally, the relatively low inductance afforded by the spaced apart, parallel connected coils allows the antenna to be tuned to resonate at typical magnetic resonance frequencies with reasonable capacitance values, including substantial capacitance in coaxial cables 132. The ability to employ coaxial cables while still permitting proper tuning is advantageous because the coaxial cables are substantially immune to stray electromagnetic signals. As in the embodiments of FIGS. 1 and 2, the orientation of apertured coils 100 and 102 with their radial directions transverse to the adjacent surface of the patient's body minimizes stray capacitance between these coils and the skin.

The antenna structure shown in FIG. 5 includes three identical apertured coils 200 all aligned on a common axis 210. Each coil 200 is generally similar to one coil 10 of the structure depicted in FIGS. 1 and 2. However, each coil 200 incorporates three concentric windings. The coils are supported in predetermined positions relative to one another by a cage-like frame similar to the frame discussed above with reference to FIGS. 3 and 4 but incorporating three annular rings 212 and no end plate. The apertures defined by the coils and rings are mutually aligned with one another so that an elongated part of a subject piece such as the leg schematically shown can be inserted through at least one of the apertures into the tubular patient receiving space 226 defined by this antenna structure. Cushions 228 are disposed in the gaps between the coils. Structures of this nature are particularly suitable for imaging elongated subjects or parts of subjects such as the limbs of a living body. Antenna structures including three aligned coils provide a particularly good sensitivity distribution in the area encompassed by the coils 200 at the axial ends of the structure. The sensitivity distribution of a coil of this type is akin to that achieved by a long helical solenoid. However, the inductance of the antenna structure according to this aspect of the invention ordinarily is lower than a solenoid having comparable sensitivity and sensitivity distribution. Here again, the helical coils are connected in parallel to one another, thus minimizing the inductance of the structure. Also, the substantial gaps between the coils further tend to minimize the inductance of the structure of a whole.

Figure 6:
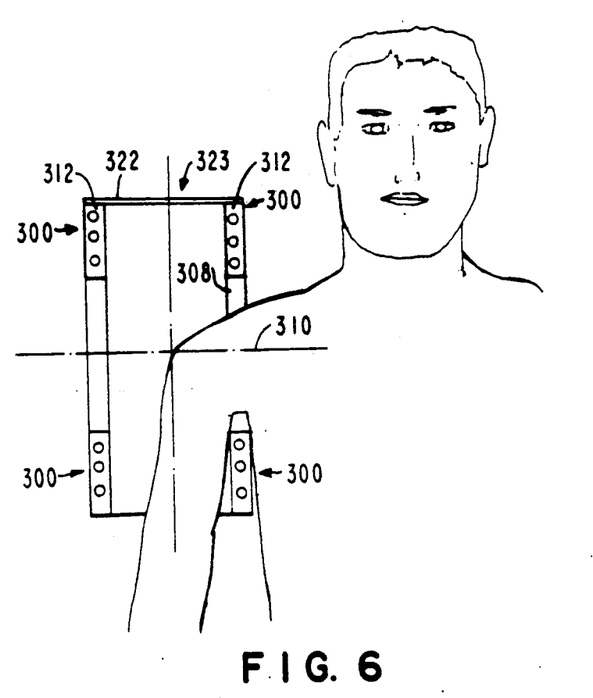

As illustrated in FIG. 6, a further antenna structure includes two apertured coils 300 and a frame 323 including apertured rings 312 and bars 322. The central aperture 308 of at least one coil 300 is unoccluded. Further, the bars 322 are spaced apart from one another around the circumference of the annular rings and apertured coils. Therefore, a substantial L-shaped body structure such as a shoulder and upper arm may be positioned in the patient receiving space 326 of this antenna structure between the coils, with one branch (the shoulder blade) extending along the axis 310 of the coils and another branch (the upper arm) extending through the gap between the coils and between bars 322. This further illustrates the positioning versatility of coil arrangements according to this aspect of the invention. Further, the deep structures of the shoulder joint are disposed immediately adjacent the common axis 310 of the coils, and adjacent the midpoint of the gap between the coils. The antenna provides particularly good sensitivity for imaging these regions.

Figure 7:
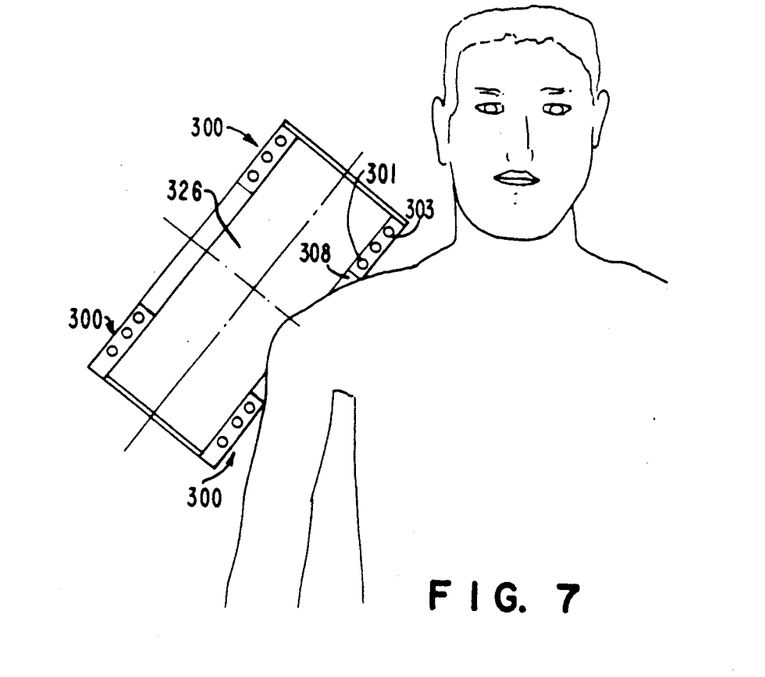
FIG. 7 is a schematic sectional view showing the antenna of FIG. 6 in a different position relative to the subject.

As shown in FIG. 7, the antenna structure of FIG. 6 can also be employed with a body part such as the shoulder of the patient protruding into patient receiving space 326 via the aperture 308 in one of the coils 300, but not protruding through any other aperture or gap in the antenna structure. Thus, the generally L-shaped shoulder can be positioned with both branches of the L extending through one aperture, as seen in FIG. 7. Although the plane of the coil is not perpendicular to the surface of the patient's body in the position of FIG. 7, the innermost turn 301 nonetheless lies closer to the body surface than does the outermost turn 303 of the same coil.

Figure 8:
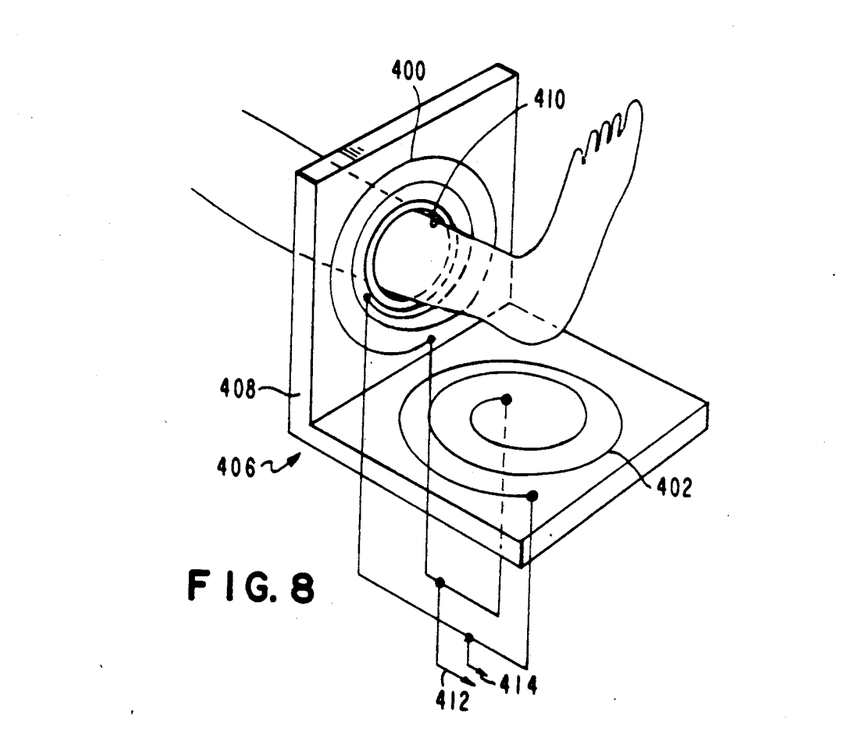
FIG. 8 is a schematic perspective view depicting an antenna in accordance with yet another embodiment of the invention.

An antenna structure according to another embodiment of the invention, as shown in FIG. 8 incorporates two spiral coils 400 and 402 mounted on a generally L-shaped frame so that the planes of the two coils are substantially perpendicular to one another. The plate 408 of frame 406 which holds coil 400 is provided with an aperture 410 adjacent the axis of coil 400. A portion of the patient's body such as the foot illustrated may be positioned through this aperture such that magnetic resonance signals from this portion of the patient's body will impinge upon both coils 400 and 402 and signals received by both coils will reinforce one another and add to the magnitude of the signals appearing at common terminals 412 and 414. Once again, coils 400 and 402 desirably are positioned within interactive range of one another as described above. However, the coils do not substantially overlap one another. This arrangement further illustrates the versatility of coil structures according to the broad compass of the present invention.

The antenna structures discussed above typically are made in sizes to fit the normal human anatomy, e.g., to fit the head or limbs of a human subject. However, the size of the antenna structure can be altered to suit other subjects. The features described above can be varied considerably within the broad scope of the invention. In an alternate arrangement, one or more of the spiral coils can be disconnected from the other coil and connected in an independent passive resonant circuit. Thus, in the arrangement of FIGS. 1 and 2 coil 24 can be disconnected from outputs 36 and 38, and hence disconnected from coil 10, and the disconnected coil 24 may be connected across a capacitor (not shown) selected to form, with coil 24, a circuit resonant at the frequencies of interest. In this arrangement capacitor 40 is exchanged for a larger capacitor so that the new capacitor forms a similarly resonant circuit with coil 10. Even though the second coil 24 is disconnected from antenna input terminals 42 and 44, the system still provides relatively good sensitivity. In particular, such an arrangement provides sensitivity at locations axially remote from coil 10 better than that achieved when coil 24 is simply removed from the system. This result suggests that a transformer effect or inductive coupling between the two coils does indeed enhance the uniform sensitivity of the system. However, optimum sensitivity is achieved when both coils are connected to the receiver terminals.

In the embodiments discussed above, the turns of each coil are constituted by a generally flat, striplike, metallic conductor lying substantially in the plane of the coil. Although such flat, striplike conductors are preferred for the reasons discussed above in most applications, other conductors may be employed. For example, the conductor may be a round, solid or tubular conductor.

As these and other variations and combinations of the features discussed above can be employed, the foregoing description of the preferred embodiments should be taken by way of illustration rather than by way of limitation of the present invention as defined by the claims.

We claim:

1. A method of magnetic resonance imaging comprising the steps of:
    (a) providing an antenna including a first spiral coil having an axis, having radial directions orthogonal to said axis and including a plurality of turns of progressively varying radial extent, an innermost one of said turns defining an aperture surrounding said axis;
    (b) juxtaposing said first spiral coil with the body of a subject so that a part of the body extends through said aperture, and the turns of said first spiral coil encircle said part of said subject's body whereby the turns of said first spiral coil having progressively larger radial extent are disposed at progressively greater distances from the surface of the encircled body part;
    (c) extending nuclear magnetic resonance in the body of said subject;
    (d) receiving magnetic resonance signals from said subject by means of said antenna; and,
    (e) reconstructing an image of at least a portion of said body part of said subject from said received resonance signals.

2. A method as claimed in claim 1 wherein said antenna includes a second spiral coil also having an axis, having radial directions orthogonal to said axis and having a plurality of turns of progressively varying radial extent, the method of further comprising the step of juxtaposing said second spiral coil with the body of the subject within interactive range of said first spiral coil, said step of receiving said magnetic resonance signals including the step of receiving said signals through both of said coils.

3. A method as claimed in claim 2 wherein the steps of juxtaposing said coils with the body of said subject are performed so that the axes of said coils lie substantially parallel to one another and said coils are spaced axially apart from one another.

4. A method as claimed in claim 3 wherein said juxtaposing steps are performed so that said coils are substantially coaxial.

5. A method as claimed in claim 3 wherein said body part is enlongated and said second spiral coil defines an aperture adjacent its axis and said juxtaposing steps are performed so that the elongated part of the subject's body extends through the apertures of both of said spiral coils.

6. A method as claimed in claim 3 wherein said body part is generally L-shaped and said juxtaposing steps are performed by positioning a generally L-shaped body part so that one branch of the L-shaped part extends through the aperture in the first spiral coil and the other branch of the L-shaped part extends through the gap between the coils.

7. A method as claimed in claim 3 wherein said body part has a proximal-to-distal axis and a distal surface generally transverse to said proximal-to-distal axis, and said step of juxtaposing said second spiral coil with the body part includes the step of positioning said second spiral coil distal to the distal surface of said body part.

8. A method as claimed in claim 7 wherein said body part is the head of the subject and said second spiral coil is positioned to overlie the top surface of the head.

9. A method as claimed in claim 7 wherein said second spiral coil has one or more inner turns adjacent its axis and said juxtaposing steps are performed so that the inner turns of said second spiral coil are aligned with the aperture of said first spiral coil.

10. A method as claimed in claim 9 further comprising the step of juxtaposing a third coil with said body part so that said third coil encircles said body part proximally of said first spiral coil, said step of receiving said signals including the step of receiving said signals through said third coil in addition to said first and second coil.

11. A method as claimed in claim 2 wherein said juxtaposing steps are performed so that said coils substantially overlap one another.

12. A method as claimed in claim 2 wherein said juxtaposing steps include the step of juxtaposing said coils with the body so that said two coils are disposed at a center to center distance less than about one times the maximum radial extent of each of said two coils.

13. A method as claimed in claim 2 wherein said coils are physically connected to one another so that said coils constitute parts of a single structure and said juxtaposing steps are performed by juxtaposing said structure with the body of the subject.

14. A receiving antenna for a magnetic resonance imaging system comprising:
(a) a first spiral coil having an axis, radial directions transverse to said axis, an aperture adjacent the axis and a plurality of turns of progressively varying radial extent encircling the aperture;
(b) means adapted for positioning said first spiral coil adjacent a part of the body of a subject to be imaged so that the body part extends through the aperture and turns of said first spiral coil encircle the body part whereby turns having progressively larger radial extent will be disposed at progressively greater distances from the encircled part; and,
(c) means for providing and electrical connections from said first spiral coil to a radio receiver.

15. An antenna as claimed in claim 14 further comprising a second spiral coil having an axis, radial directions transverse to the axis and a plurality of turns of progressively varying radial extent, said adapted for positioning further positioning said second spiral coil adjacent the body of the subject within interactive range of said first spiral coil.

16. An antenna as claimed in claim 15 further comprising means for electrically interconnecting said second coil and said first coil, said means for providing an electrical connection further connecting said second spiral coil to the radio receiver.

17. An antenna as claimed in claim 16 wherein said second coil has one or more inner turns adjacent its axis, the inner turns of said second coil being aligned with the aperture in said first coil.

18. An antenna as claimed in claim 17 further comprising a third coil defining an aperture aligned with said aperture of said first coil, said third coil being disposed axially between said first and second coils.

19. An antenna as claimed in claim 15 wherein said means adapted for positioning includes a frame, said coils being mounted to said frame so that said coils and said frame cooperatively define a structure having a patient receiving space between said coils, whereby the aperture in said first coil provides an opening for insertion of the part of a patient's body into said patient receiving space of said structure.

20. An antenna as claimed in claim 19 wherein the axes of said coils are substantially parallel to one another, said coils substantially overlapping one another and being spaced apart from one another in the axial directions of the coils.

21. An antenna as claimed in claim 20 wherein said coils are substantially coaxial with one another.

22. An antenna as claimed in claim 20 wherein said body part is elongated and said second coil has an aperture adjacent its axis, said apertures being aligned with one another, whereby the elongated part of a patient's body can be inserted through said aligned apertures.

23. An antenna as claimed in claim 22 further comprising a third coil mounted to said frame and axially spaced from said first and second coils, said 24. An antenna as claimed in claim 20 wherein said body part is generally L-shaped and said structure defines an intercoil opening between one said aperture coil and the adjacent coil, whereby said generally L-shaped region of the patient's body may be positioned in said structure with one branch of the L-shaped region extending through said aperture in the axial direction of said coils and another branch of said L-shaped region extending generally radially with respect to said coils through said intercoil space, and the juncture of these branches at the corner of the L-shaped region, being positioned within said patient receiving space adjacent to the axis of said coils and axially between said coils.

25. An antenna as claimed in claim 20 wherein said first coil is substantially planar, the plane of said first coil being substantially perpendicular to the axis of the coil.

26. An antenna as claimed in claim 15 wherein said means adapted for positioning said coils adjacent the body of the patient includes means for positioning said coils in a preselected orientation with respect to one another and further comprising means for electrically interconnecting said coils to one another so that upon passage of a current through each of said interconnected coils the resulting magnetic flux from one of said coils will reinforce the magnetic flux from the other one of said coils at least within a region of the subject's body disposed between said coils.

* * * * *

UNITED STATES PATENT AND TRADEMARK OFFICE
CERTIFICATE OF CORRECTION

PATENT NO. : 5,050,605
DATED : September 24, 1991
INVENTOR(S) : Eydelman et al

It is certified that error appears in the above-identified patent and that said Letters Patent is hereby corrected as shown below:

```
Column 6, line 68, "Pr" should read --Pr--.
Column 7, line 4, "PR" should read --Pr--.
Column 14, line 37, "extent" should read --extents--.
Column 14, line 40, "extending" should read --exciting--.
Column 15, line 5 "positioning a" should read --positioning the--.
Column 15, line 59, after "encircled" insert --body--.
Column 15, line 61, "and" should read --an--.
Column 15, line 61 "connections" should read --connection--.
Column 15, line 66, after "said" insert --means--.
Column 16, line 17, "means adapted" should read --adapted means--.
Column 16, line 38 after "second coils, said" insert -- third coil
defining an aperture aligned with said apertures of said first and
second coils. --
```

Signed and Sealed this

Twenty-fifth Day of May, 1993

Attest:

MICHAEL K. KIRK

*Attesting Officer*    Acting Commissioner of Patents and Trademarks